United States Patent [19]

Hermeling et al.

[11] Patent Number: 5,009,753

[45] Date of Patent: Apr. 23, 1991

[54] PREPARATION OF DIHYDROXYDIONES

[75] Inventors: Dieter Hermeling, Neustadt; Rainer Becker, Bad Durkheim; Walter Dobler, Heidelberg, all of Fed. Rep. of Germany

[73] Assignee: BASF Aktiengesellschaft, Ludwigshafen, Fed. Rep. of Germany

[21] Appl. No.: 423,224

[22] Filed: Oct. 18, 1989

[30] Foreign Application Priority Data

Nov. 9, 1988 [DE] Fed. Rep. of Germany ....... 3837954

[51] Int. Cl.$^5$ ................................................ C25B 3/00
[52] U.S. Cl. ......................................... 204/75; 204/76; 204/73 R
[58] Field of Search ................... 204/72, 73 R, 75, 76

[56] References Cited

U.S. PATENT DOCUMENTS

| | | | |
|---|---|---|---|
| 3,984,294 | 10/1976 | Nohe et al. | 204/76 |
| 4,087,336 | 5/1978 | Wagenknecht | 204/75 |
| 4,133,729 | 1/1979 | King | 204/73 R |
| 4,157,286 | 6/1979 | King | 204/73 R |

OTHER PUBLICATIONS

Baizer et al., "Organic Electrochemistry", Second Edition, Marcel Dekker, Inc., N.Y., 1983, pp. 652–653.
J. Chem. Soc., Perkin Trans. I (1985), 795.
J. Org. Chem. 43, 4245 (1978).
J. Org. Chem. 38, 123 (1973).
Coll. Czech. Chem. Commun. 32 (1967), 1497–1504.

Primary Examiner—John F. Niebling
Assistant Examiner—Steven P. Marquis
Attorney, Agent, or Firm—John H. Shurtleff

[57] ABSTRACT

Dihydroxydiones of the general formula

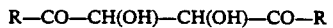

R—CO—CH(OH)—CH(OH)—CO—R    I where R is alkyl, are prepared by a process in which an aldehyde of the general formula

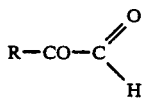

II where R has the abovementioned meaning, is subjected to electrolysis in a water-containing electrolyte which has a pH of less than 7.

8 Claims, No Drawings

PREPARATION OF DIHYDROXYDIONES

The present invention relates to a novel electrochemical process for the preparation of dihydroxydiones, such as 3,4-dihydroxyhexane-2,5-diones.

Several processes have been proposed for the preparation of 3,4-dihydroxyhexane-2,5-dione. For example, according to J. Chem. Soc. Perkin Trans. I (1985), 795, 3,4-dihydroxyhexane-2,5-dione is obtained in a multistage synthesis. J. Org. Chem. 43 (1978), 4245 and J. Org. Chem. 38 (1973), 123 disclose that this compound is obtained by a single-stage or multistage oxidation of 2,5-dimethylfuran with potassium chlorate or osmium tetroxide. The fact that 2,5-dimethylfuran is expensive and the explosive and toxic oxidizing agents are difficult to handle prevents industrial use. Finally, the reduction of methyl glyoxal to 3,4-dihydroxyhexane-2,5-dione with zinc, which is described in J. Org. Chem. 38 (1973), 123, is also disadvantageous owing to the problems involved in having to dispose of the zinc wastes produced.

It is an object of the present invention to provide a process which permits the preparation of dihydroxydiones, such as 3,4-dihydroxyhe-xane-2,5-dione, in a more advantageous manner.

We have found that this object is achieved by the process of this invention, in which dihydroxydiones of the general formula

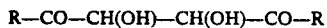

R—CO—CH(OH)—CH(OH)—CO—R     I where R is alkyl, are prepared by subjecting an aldehyde of the general formula

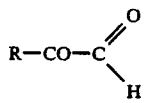

where R has the abovementioned meaning, to electrolysis in a water-containing electrolyte which has a pH of less than 7.

The aldehydes of the formula II contain alkyl of, for example, 1 to 6, preferably 1 to 4, carbon atoms as radical R. They undergo cathodic dimerization in the electrolysis according to the invention. This result could not be foreseen since Coll. Czech. Chem. 32 (1967), 1497-1504 discloses that 1,2-propanediol is formed by cathodic reduction in the electrolysis of methylglyoxal at a pH greater than 7.

The process of the invention can be carried out in both divided and undivided electrolysis cells, better yields being obtained in divided cells.

The anode materials used are, for example, noble metals, such as platinum, or metal oxides, such as $RuO_2$. Graphite is the preferred anode material. The cathodes used are, for example, iron, nickel or steel, preferably graphite or lead.

The aldehyde of the formula II is subjected to electrolysis in a water-containing electrolyte. The electrolyte should furthermore contain a conductive salt and may also contain an aliphatic alcohol, such as methanol or ethanol, and, as an acid, acetic acid. All salts which are known to be conductive salts and are substantially stable under the electrolysis conditions can be used as conductive salts. Examples of suitable conductive salts are sulfonates, for example the alkali metal salts of benzenesulfonic acids, such as $KSO_3Ph$, or acetates, such as potassium acetate or sodium acetate. The electrolyte advantageously contains acetic acid when divided cells are used and advantageously contains sodium acetate or potassium acetate when undivided cells are employed.

The electrolyte has, for example, the following composition:
from 5 to 40% by weight of an aldehyde of the formula II,
from 10 to 90% by weight of water,
from 0 to 80% by weight of methanol or ethanol,
from 0 to 50% by weight of acetic acid and
from 0.1 to 5% by weight of a conductive salt.

Its pH is less than 7, preferably from 4 to 6.

In the novel process, the current densities are from 0.5 to 25, preferably from 1 to 5, $A/dm^2$. Electrolysis is preferably carried out under atmospheric pressure and at not more than 100° C., advantageously at from 0 to 90° C., preferably from 40 to 60° C. The electrolysis can be carried out batchwise or continuously.

The dihydroxydiones can be obtained from the discharged electrolysis solution in a conventional manner, for example by extraction with an organic solvent. Since the dioldione is very soluble in water, continuous extraction, for example with ethyl acetate is advantageous. If the 3,4-dihydroxyhexane-2,5-dione obtained by the process of the invention is intended to be used for the preparation of 2,5-dimethyl-4,5-dihydrofuran-3-ol-4-one, which is a known scent, the discharged electrolysis solution can also be converted directly into the desired end product. Appropriate cyclization conditions are described in, for example, German Laid-Open Application DOS 2,845,843.

EXAMPLE

Apparatus : undivided cell having 11 electrodes
Cathode : graphite
Electrolyte:
    555 g of methylglyoxal (18.5%)
    940 g of water (31.3%)
    1,496 g of methanol (49.9%)
    9 g of sodium acetate (0.3%)
Anode : graphite
Current density: 3.3 $A/dm^2$
Temperature : from 45 to 50° C.

Electrolysis is carried out with 1 F/mole of methylglyoxal. The electrolyte is pumped via a heat exchanger at 200 l/h during electrolysis.

After the end of the electrolysis, the reacted mixture is freed from the solvent in a rotary evaporator. 391 g of oil remained, which is shown to contain 68% of 3,4-dihydroxyhexane-2,5-dione by gas chromatographic analysis. This corresponds to a yield of 47%, 69% being in the dl form and 31% in the meso form. This mixture can be used directly in the abovementioned cyclization reaction for the preparation of 2,5-dimethyl-4,5-dihydrofuran-3-ol-4-one or can be subjected to continuous extraction. Extraction for 80 hours with ethyl acetate gives 234 g of 3,4-dihydroxyhexane-2,5-dione as an isomer mixture, which can be separated by fractional crystallization. The dl form (mp: 89–91° C. from ethyl acetate/hexane) and the meso form (mp: 59–61° C. from carbon tetrachloride/chloroform are obtained.

We claim:

1. A process for the preparation of a dihydroxydione of the formula

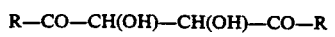

R—CO—CH(OH)—CH(OH)—CO—R     I where R is alkyl, which comprises:
subjecting an aldehyde of the formula

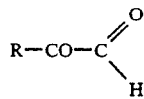

where R has the abovementioned meaning, to electrolysis in a water-containing electrolyte which has a pH of about 4 to 5 while using a cathode selected from the group consisting of graphite, lead, iron, nickel and steel.

2. A process as claimed in claim 1, wherein the electrolysis is carried out in an undivided flow-through cell.

3. A process as claimed in claim 1, wherein the electrolysis is carried out in a divided cell.

4. A process as claimed in claim 1, wherein electrolysis is carried out at a current density of from 0.5 to 25 $A/dn^2$ and at from 0 to 90° C.

5. A process as claimed in claim 1, wherein an electrolyte composed of from 5 to 40% by weight of an aldehyde of the formula II, from 10 to 90% by weight of water, from 0 to 80% by weight of methanol or ethanol, from 0 to 50% by weight of acetic acid and from 0.1 to 5% by weight of a conductive salt is used for the electrolysis.

6. A process as claimed in claim 1, wherein electrolysis is carried out at a current density of from about 1 to 5 $A/dm^2$ and at a temperature of about 40 tp 60° C.

7. A process as claimed in claim 1, wherein R is alkyl of 1 to 4 carbon atoms.

8. A process as claimed in claim 1, wherein R is methyl.

* * * * *

UNITED STATES PATENT AND TRADEMARK OFFICE
CERTIFICATE OF CORRECTION

PATENT NO. : 5,009,753
DATED : April 23, 1991
INVENTOR(S) : Hermeling et al

It is certified that error appears in the above-identified patent and that said Letters Patent is hereby corrected as shown below:

Column 4:

In Claim 4, at line 5, change "$A/dn^2$" to --$A/dm^2$--.

Signed and Sealed this

First Day of September, 1992

Attest:

DOUGLAS B. COMER

Attesting Officer

Acting Commissioner of Patents and Trademarks